US010758193B2

(12) United States Patent
Bettega (10) Patent No.: US 10,758,193 B2
(45) Date of Patent: Sep. 1, 2020

(54) MEDICAL RADIATION PROTECTOR AND PRODUCTION THEREOF

(71) Applicant: HIBRAND INDUSTRIES AG, Ruggell (LI)

(72) Inventor: Remo Bettega, Diepoldsau (CH)

(73) Assignee: HIBRAND INDUSTRIES AG, Ruggell (LI)

( * ) Notice: Subject to any disclaimer, the term of this patent is extended or adjusted under 35 U.S.C. 154(b) by 0 days.

(21) Appl. No.: 16/092,832

(22) PCT Filed: Apr. 14, 2016

(86) PCT No.: PCT/EP2016/058177
§ 371 (c)(1),
(2) Date: Oct. 11, 2018

(87) PCT Pub. No.: WO2017/178050
PCT Pub. Date: Oct. 19, 2017

(65) Prior Publication Data
US 2019/0117175 A1    Apr. 25, 2019

(51) Int. Cl.
*A61B 6/10*    (2006.01)
*A61C 13/00*    (2006.01)
(Continued)

(52) U.S. Cl.
CPC ............ *A61B 6/107* (2013.01); *A61C 9/0053* (2013.01); *A61C 13/0004* (2013.01); *A61N 5/1014* (2013.01); *A61N 2005/1094* (2013.01)

(58) Field of Classification Search
CPC ... A61C 13/0004; A61C 13/0013; A61C 7/08; A61C 8/0006; A61C 5/90; A61C 7/002;
(Continued)

(56) References Cited

U.S. PATENT DOCUMENTS 8,409,069 B1 *  4/2013  Schuman ............. A61N 5/1014
                                             600/3
9,937,019 B1 *  4/2018  Copps ...................... A61C 7/08
                        (Continued)

FOREIGN PATENT DOCUMENTS

DE    198 28 003 A1    1/2000
EP        2215967 A1    8/2010
WO    2011026662 A1    3/2011

OTHER PUBLICATIONS

International Search Report and Written Opinion dated Dec. 21, 2016 in International Application No. PCT/EP2016/058177.
(Continued)

*Primary Examiner* — David A Vanore
(74) *Attorney, Agent, or Firm* — Muncy, Geissler, Olds & Lowe, P.C.

(57) ABSTRACT

The invention relates to a medical radiation protector, which is configured in such a way that said radiation protector holds tumor tissue and adjoining healthy tissue in a clear relative position with respect to each other in the head-and-neck region during a radiation treatment for cancer therapy, and which comprises at least a lower jaw element, an upper jaw element, and optionally a tissue protection element, and which is produced partially from a plastic that can be used in an additive method and that is approved for use in/against/on a human or animal body for medical purposes, wherein the part produced from said plastic is produced by means of an additive production method. The invention further relates to a production method for said radiation protector, to a system for performing the method, and to a computer program that substantially controls the method.

18 Claims, 7 Drawing Sheets

(51) Int. Cl.
*A61N 5/10* (2006.01)
*A61C 9/00* (2006.01)

(58) Field of Classification Search
CPC ......... A61C 7/146; A61C 7/36; A61C 8/0009;
B33Y 80/00; B33Y 10/00; A61L 2430/12;
A61L 27/3865; A61N 2005/1094; A61N
5/10; A61N 5/1014; A61N 2005/1097;
A61B 1/24; A61B 5/0062; A61B 5/0088
USPC ............... 128/859; 700/98; 250/515.1, 516.1
See application file for complete search history.

(56) References Cited

U.S. PATENT DOCUMENTS

| | | | | |
|---|---|---|---|---|
| 2008/0090207 | A1* | 4/2008 | Rubbert | A61C 8/0036 433/171 |
| 2008/0090208 | A1* | 4/2008 | Rubbert | A61C 13/0004 433/173 |
| 2010/0292526 | A1* | 11/2010 | Schuman | B29C 64/135 600/3 |
| 2011/0026662 | A1 | 2/2011 | di Bari et al. | |
| 2012/0064489 | A1* | 3/2012 | Rubbert | A61C 8/0006 433/175 |
| 2012/0065756 | A1* | 3/2012 | Rubbert | A61C 8/0012 700/98 |
| 2012/0167897 | A1* | 7/2012 | Bettega | A61B 6/107 128/860 |
| 2016/0374784 | A1* | 12/2016 | Joshi | A61B 6/032 433/214 |
| 2017/0007359 | A1* | 1/2017 | Kopelman | A61C 7/08 |
| 2018/0028063 | A1* | 2/2018 | Elbaz | A61B 5/0088 |
| 2019/0282331 | A1* | 9/2019 | Rubbert | A61K 6/58 |
| 2019/0282345 | A1* | 9/2019 | Friebauer | A61O 5/007 |
| 2019/0374309 | A1* | 12/2019 | Parkar | B29C 64/20 |

OTHER PUBLICATIONS

Hibrand Industries Ag: "Intraoral Protector Designer", Apr. 12, 2016, XP055326905, Gefunden im Internet: URL:htpp://neu.hibrand.li/images/catalogue/intra-oral-protector.pdf [gefunden am Dec. 7, 2016] Seite 1-Seite 39.

Zemnick et al: "Rapid prototyping technique for creating a radiation shield", Journal of Prosthetic Dentistry, Elsevier, Amsterdam, NL, Bd. 97, Nr. 4, Apr. 1, 2007 (Apr. 1, 2017), Seiten 236-241, XP022072774, ISSN: 0022-3913, DOI: 10.1016/J. PROSDENT 2007.02.005 Seite 236-Seite 241.

"Biological Evaluation of Medical Devices—Part 1: "Evaluation and Testing within a Risk Management Process" EN ISO 10993-1:2009".

"Blue Book Memorandum G 95-1 / FDA Draft Guidance" of Apr. 23, 2013 EN ISO 10993-1:2009.

International Search Report dated Dec. 21, 2016 in corresponding application PCT/EP2016/058177.

International Preliminary Report on Patentability dated Oct. 16, 2018 in corresponding application PCT/EP2016/058177.

Hilbrand Industries Ag: "Intraoral Protector Designer", Apr. 12, 2016, XP055326905, Retrieved from the internet: URL: http??neu.hibrand.li/images/catalogue/intra-oral-protector.pdf [retrieved on Dec. 7, 2016].

Zemnick et al: "Rapid prototyping technique for creating a radiation shield", Journal of Prosthetic Dentistry, Elsevier, Amsterdam, NL, vol. 97, No. 4, Apr. 1, 2007, pp. 236-241, XP022072774, ISSN: 0022-3913, DOI: 10.1016/ J.PROSDENT, 2007.02.005.

* cited by examiner

MEDICAL RADIATION PROTECTOR AND PRODUCTION THEREOF

This application is a 371 National Phase of PCT Application No. PCT/EP2016/058177, filed on Apr. 14, 2016; and which is herein incorporated by reference in its entirety.

The present application relates to a medical radiation protector for the protection of the healthy tissue surrounding the tumor in radiation treatments as carried out for cancer, as well as its production, a computer program product for its manufacture and a system for the same purpose.

Protectors of the type mentioned above are known from the same inventor from WO 2011/026662 A1 and EP 2215967 A1 for use in carcinomas in the head-and-neck region. The radiation protectors prevent damage to healthy tissue in the surrounding area of the irradiated tumor, in the context of tele- or brachytherapy, i.e. irradiation with a radiation source outside the body or in or directly on the body. For the production of the radiation protectors described in the aforementioned documents, an impression of the dental cavity is made in the conventional manner, e.g. using alginate impression material. Based on this, a plaster cast is made as a jaw relation record and the position of the upper and lower jaws is determined in a central position in an articulator. A plastic material is modelled onto the plaster model fixed in the articulator, which is then shaped into the final shape of the radiation protector after curing by milling and subsequent polishing. In this case, a tongue element, cheek elements and/or lip elements can be integrally formed, which ensure that the radiation protector keeps the healthy tongue, cheek and/or lip tissue reproducibly away from the beam path or the tumor tissue to be irradiated in a defined position. In addition, anchorages in the form of press studs can be incorporated into the radiation protector for anchoring lead plates used for radiation shielding. Catheter channels can also be provided to accommodate wires or tubes whose tips are provided with radiating material so that the radiating material can be positioned in relation to the tumor in a reproducible manner in the body or directly on the tumor. Unfortunately, the manufacture of the radiation protector described here involves a great deal of manual effort, which makes the manufacturing process both time-consuming and expensive.

Also known from US 2010/0292526 A1 is a radiation protector for brachytherapy of the oral cavity, which is made of plastic and provided with a catheter channel for positioning the radiation source. The radiation protector, which is formed in mirror-image to the upper or lower jaw of the patient, is cast in the conventional manner from a dental methyl methacrylate, for example. Lead can be enclosed in the material of the radiation protector, for example by casting it in. Another way of manufacturing is based on a 3 dimensional (3D) computer model, which is created by CT scanner, MDCT scanner or dental (cone-beam) scanner skull area. The dental cone beam scanner also works with a CT procedure, which generates sectional images at least of the oral cavity area of the skull and in particular of its hard tissue, i.e. teeth and bones. Based on this 3D computer model, the radiation protector is manufactured from a photopolymer by a computer-controlled lithographic process or from polyurethane by means of a computer-controlled milling process. Although this method considerably reduces the manual work by using a 3D computer model of the oral cavity, the effort for the creation of the 3D computer model by means of CT is very complex and expensive and additionally burdens the patient with X-rays.

As an alternative to the radiation protectors presented above and their manufacturing processes, the radiation protector presented here can be manufactured simply, quickly and inexpensively and still enables an individual design adapted to each individual patient and their needs.

The method presented here for producing a medical radiation protector configured to keep tumor tissue and adjacent healthy tissue in a unique relative position to each other during a cancer therapy radiation treatment in the head-and-neck area includes the creation of a 3D computer model of the patient's oral cavity using a scanner, wherein the scanner works with a light-based measurement method and measures the patient's oral cavity in its three dimensions. From the resulting scanner data, a 3D image file of the surfaces of the patient's oral cavity is generated in a computing unit, wherein a 3D image can be displayed on a screen from the 3D image file. This enables quality control of the scan. From the 3D image file or the 3D image of the surfaces of the patient's oral cavity, a virtual 3D solid model (Volumenmodell) of the radiation protector is generated with the aid of the computer unit, which can also be displayed on a screen. Optionally, the virtual 3D solid model of the radiation protector can be adapted to the individual needs of the patient and his treatment by manual intervention with the aid of the computer unit. A resulting virtual 3D model or the virtual 3D solid model of the radiation protector is transformed into a control file for controlling a device to carry out an additive manufacturing method and the device is fed with the necessary materials. Finally, the device is controlled by the control file and the radiation protector is manufactured using the device in an additive manufacturing method. (In the following, the term "device for carrying out an additive manufacturing method" is often simply used in a shorter form by using the term "device").

The measurement of the oral cavity by means of a light-based measurement method and a scanner configured for this purpose enables a very cost-effective and fast measurement of the same without the patient being exposed to X-rays or high-density magnetic fields. There is also no need to take alginate impressions of the upper and lower jaw, which most patients find very unpleasant.

An LED scanner or a laser scanner is advantageously used as scanner.

Scanner data in the form of a 3D point cloud are advantageously obtained from a light-based measurement.

The scan is advantageously performed with the mouth open, wherein the upper and lower jaw are brought into a position fixed to each other, especially with the aid of a retractor. For a more precise generation of a 3D solid model of the radiation protector, it is also advantageous to scan those elements that hold the jaw in position, for example individual spreading elements in the mouth that hold the mouth open or parts of the retractor in the mouth. When optimizing the 3D image data, the data of these scanned elements can then be specifically ignored. The data of upper jaw scan and lower jaw scan can—with known, i.e. measured spreading elements/retractor elements—be brought much more precisely into anatomical compliance, so that an anatomically more accurate 3D image of the surfaces of the oral cavity and their mutual position can be generated, e.g. for the closed mouth with teeth lying on top of one another or almost lying on top of one another. Depending on various factors, such as location and dimension of the tumor, possibilities of the scanner and the software, anatomical characteristics of the patient, etc., it is more advantageous or even necessary to make a separate scan from the upper and lower jaw areas and possibly also from the spreading elements/refractor elements to make a separate scan and then to merge the data of the different scans into a 3D image of the surfaces, wherein, as already mentioned above, the data of the spreading elements/refractor elements are specifically ignored.

The 3D image data and the 3D image are optimized advantageously with the aid of the computer unit in such a way that missing data are added and superfluous data and obviously incorrect measured values are not taken into account. This optimization, as well as the merging of data from separate scans into a 3D image described in the previous paragraph, is automatically executed by a corresponding program part of a computer program used to carry out the manufacturing process, wherein it is advantageous to output the result on a screen so that the result can be checked. It is also advantageous to provide a communication interface via which a user can communicate with the processing unit. This can take place, for example, in the form of a selection menu on the screen, which allows further optimization either manually or, for example, also by changing certain parameters, e.g. limit values for the definition of faulty measured values, etc., and/or by executing the optimization program section again.

The use of an additive manufacturing method and a device designed for this purpose allows not only a relatively time- and cost-efficient production of the radiation protector, but also the realization of more complex structures, without individual interlocking parts of the radiation protector having to be manufactured separately and then assembled, as was the case in the past. However, the mutual positioning of the joined parts is less reproducible, which also reduces the reproducibility of the exact position of the different tissues. With the additive manufacturing method, all elements can be manufactured in one piece from the processable material, which improves the reproducibility and accuracy of positioning.

By means of the additive manufacturing method, a plastic which is approved for medical purposes for use in/at/on a human or animal body is advantageously applied in layers or in individual material lines or in other words in individual material traces. These special designs of the additive process have the advantage of generating little waste and also being able to produce structural elements with very fine, small dimensions in the often necessary complexity and this cost-effectively with a relatively advantageous amount of time required.

Even pocket-shaped recesses or catheters for accommodating another element or other material can be easily and quickly integrated into the radiation protector with the aid of the additive manufacturing method and in particular with the process working in layers or with traces of material.

A computer program product with program code stored on a machine-readable carrier or computer data signal embodied by an electromagnetic wave for carrying out the method described above, in particular on a system as described below, comprises various program units, namely: a program unit for controlling the scanner and for creating and optionally storing scanner data resulting from the scan, a program unit for creating and optionally storing a 3D image file or 3D image of the surface of the patient's oral cavity generated from the scanner data, in particular with optimized image data, a program unit for creating and optionally storing a 3D solid model of the radiation protector from the 3D image data or the optimized 3D image data, a program unit for optionally adapting the 3D solid model to the individual needs of the patient and the treatment of the patient and storing the resulting 3D model, a program unit for transforming the 3D model of the radiation protector or the 3D solid model into a control file for controlling a device for carrying out an additive manufacturing method and optionally an interface for transferring and executing the control file on a device for carrying out an additive manufacturing method. The interface for executing the control file is software that enables the control file to actually control the device in such a way that the additive manufacturing method can be carried out on it, such as a data protocol, software for controlling a hardware interface, a printer driver, software for transformation into a printer language.

It is advantageous to store the individual program units separately from each other and to execute them separately.

For carrying out the method as described above, a system is provided, comprising a scanner for performing a measurement method and a device for carrying out an additive manufacturing method (hereinafter referred to as a device), configured to process a plastic approved for medical use in/at/on a human or animal body and a computer unit connected to the scanner and the device, a communication interface and a display screen, and configured to perform the functions of the program units described above. Computer unit, scanner, device, communication interface and screen are also referred to as the apparatuses of the system, but this is not to be understood as an exhaustive list.

It goes without saying that the apparatuses of the system have hardware interfaces which allow data exchange or communication between the apparatuses and that the system as a whole, in particular the computer unit or sub-units of these software interfaces, which together with the hardware interfaces enable data exchange or communication between the apparatuses.

In a special embodiment, the computer unit is split into individual sub-units. This has the advantage that the sub-units can be integrated into different apparatuses of the system. Sub-units, which serve to control the scanner and/or to process the scanner data, are then integrated into the scanner, for example. Alternatively or additionally, sub-units which serve to control the additive manufacturing method and/or sub-units which serve to transform a 3D model or 3D solid model into a control file for controlling such a method are integrated into the corresponding device for executing the additive manufacturing method.

The device for carrying out the additive manufacturing method is advantageously a device for the layered application of material or a device for the trackwise application of material or applications of material in lines. The material is preferably one or more plastics of the type described above, or in other words one or more different plastics with the properties described above.

As described above, the scanner is a scanner for carrying out a light-based measurement method, in particular an LED scanner or a laser scanner, wherein a 3D point cloud is preferably generated from the method.

A medical radiation protector configured to hold tumor tissue and adjacent healthy tissue in a well defined relative position to each other during a cancer therapy radiation treatment in the head-and-neck region, comprises at least one lower jaw element, an upper jaw element, and optionally a tissue protection element, wherein the lower jaw element and the upper jaw element serve a unique relative positioning of the upper jaw and the lower jaw to each other and the tissue protection element serves to protect at least one further tissue in the oral cavity region. Such a protector is known in its basic structure with lower jaw element, upper jaw element and with a tissue protection element in the form of a tongue hold-down from EP 2215967 A1 (see FIG. 1 and sections[0020] and [0021]) originating from the same inventor and also from WO 2011/026662 A1, which originates from the same inventor, wherein not only a tongue positioner but also a lip positioner and a cheek positioner are described there as tissue protection elements (see FIGS. 1, 6, 7, 8 and associated descriptions and page 5 line 12 to page 6 line 26). The structural features described there are expressly referred to and with this quotation they are integrated into this application as an independent component, so that a more precise description of the structural features of the radiation protector is dispensed with here. However, the radiation protectors described in the cited applications are manufactured in a much more complex, time-consuming and cost-intensive manner, as described above. The radiation protector presented here has the same structural elements, namely the lower and upper jaw elements and optionally a tissue protection element, but it is at least partially made of a plastic which can be used in an additive method and is approved for medical purposes for use in/at/on a human or animal body, wherein the part of the radiation protector made of this plastic is also produced by means of an additive manufacturing method.

The plastic advantageously has a tolerance in contact with the skin or mucous membrane of at least 24 hours, wherein this compatibility is defined at least according to EN ISO 10993-1:2009 "Biological Evaluation of Medical Devices—Part 1: "Evaluation and Testing within a Risk Management Process" or according to the "Blue Book Memorandum G 95-1/FDA Draft Guidance" of April 2013.

The part of the protector produced by the additive process is manufactured as described above either in layers from individual material lines or in other words from individual material tracks, with the corresponding advantages described.

The radiation protector can optionally comprise at least one other material from the following group in addition to the aforementioned plastic: another plastic, a radiation-shielding material, a radiating material. These materials can be integrated into the radiation protector during the additive manufacturing method if the device is able to do so, or they are subsequently inserted into the catheters or pocket-shaped recesses, the latter possibly only immediately before treatment, which has obvious advantages especially for radiating material.

As already partially mentioned above, the tissue protection element can be an element from the group of the following elements: a tongue positioner, a cheek positioner, a lip positioner, a mouthguard, a catheter or a pocket-like recess for receiving another element or another material. In this case, catheters and pocket-like recesses are advantageously incorporated during the additive manufacturing method.

The tongue positioners, cheek positioners, lip positioners serve a clear positioning of tongue, lip and cheek tissue relative to the upper and lower jaw. Catheters and pocket-like recesses are used to accommodate a further element or material such as the radiation source (wire or tube with radiating material at its tip) or a radiation-shielding material, i.e. a lead plate or a lead foil. Lead plate and lead foil can also be part of a mouthguard, so that a corresponding recess is provided in the area of the teeth to be protected, for example, which together with the lead foil or lead plate placed inside forms the mouthguard. Normally, the recess will have an opening so that the additional element or material can be inserted and removed through this opening into the radiation protector. Under certain circumstances, however, the additional element/material, such as the lead foil or lead plate, can also be incorporated into the radiation protector during the additive manufacturing method, so that the pocket-like recess for such an element/material is completely closed.

It is advantageous that at least the upper jaw element and lower jaw element are manufactured integrally with one another. It is even better when the upper jaw element and lower jaw element and all tissue protection elements are manufactured in one piece, since all elements are then arranged in a fixed position relative to each other and thus also during the treatment for a reproducible arrangement of tissues relative to each other and—when the radiation source is supplied by catheter or into a recess—also relative to the radiation source.

If the radiation protector is manufactured using the additive method, and if the preparatory work has been carried out using the method described above, the radiation protector can be produced more cost-effectively and more quickly and with less strain on the patient.

The invention is described in more detail below using the exemplary embodiments shown in the drawings. The explanations are only exemplary and have no restrictive effect. Identical elements are marked with identical reference numerals in the figures. The figures show purely schematically:

Figure 1:
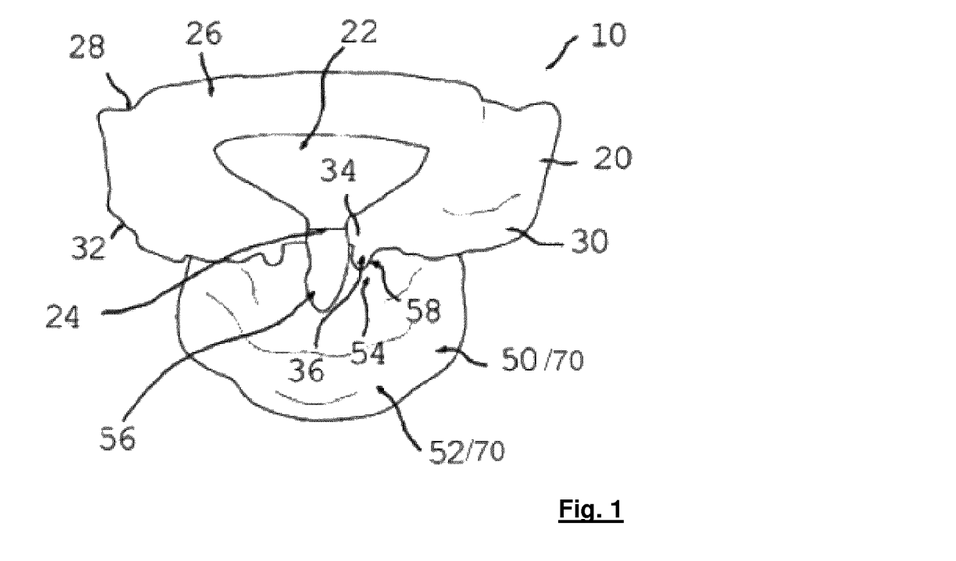
FIG. 1 the radiation protector as known from WO2011/026662.

FIG. 1 shows the radiation protector 10 from WO 2011/026662 from the same inventor. On page 11, line 29 to page 13, line 2 of WO 2011/026662, the radiation protector 10 is described in more detail. It has an upper jaw element 20/26 with an upper tooth support 28 and a lower jaw element 30 with a lower tooth support 32. It also includes a tongue positioner 50/52 as a tissue protection element 70. Tongue positioner 50/52 and lower jaw element 30 are connected to each other via a matrix 54 patrix 34 connection. Since the radiation protector 10 used here is preferably designed in one piece, it preferably does not require any matrices 54/patrices 34 or similar connecting elements. It may contain such elements, but does not have to contain such elements. Since the radiation protector 10 used here basically has the same structural elements as the one from WO 2011/026662, no further details are described here.

Figure 2:
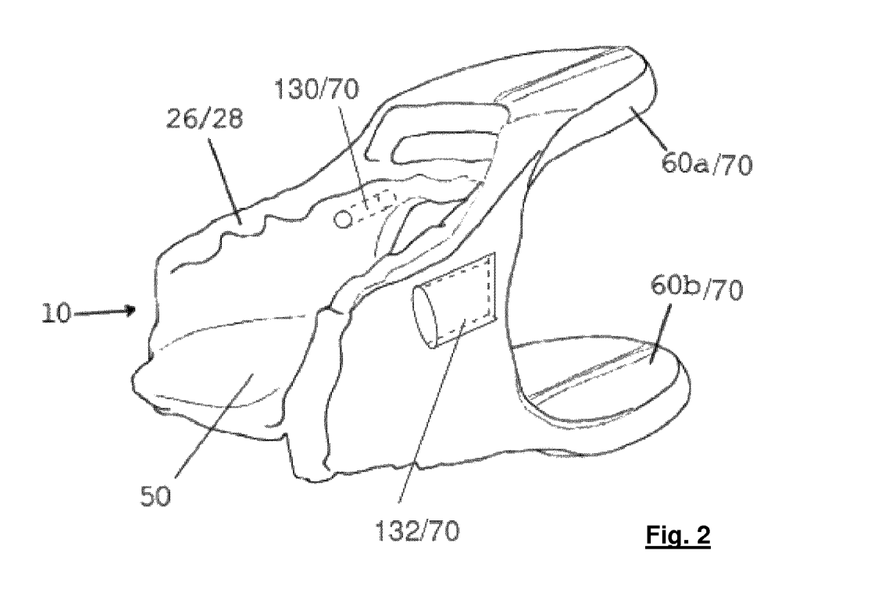
FIG. 2 a radiation protector with tissue protection elements.

FIG. 2 shows a radiation protector 10, which is designed similar to that of FIG. 1, except that the radiation protector 10 also comprises two lip positioners, namely lip positioner 60*a* for the upper lip and lip positioner 60*b* for the lower lip, as well as a catheter 130 and a pocket-shaped recess 132 as tissue protection elements 70. The shown radiation protector 10 is formed together with all tissue protection elements 70 in one piece during the additive manufacturing method. No manual milling is necessary to create recesses 132, catheter 130, pushbuttons or latching elements for snap mechanisms or similar.

Figure 3:
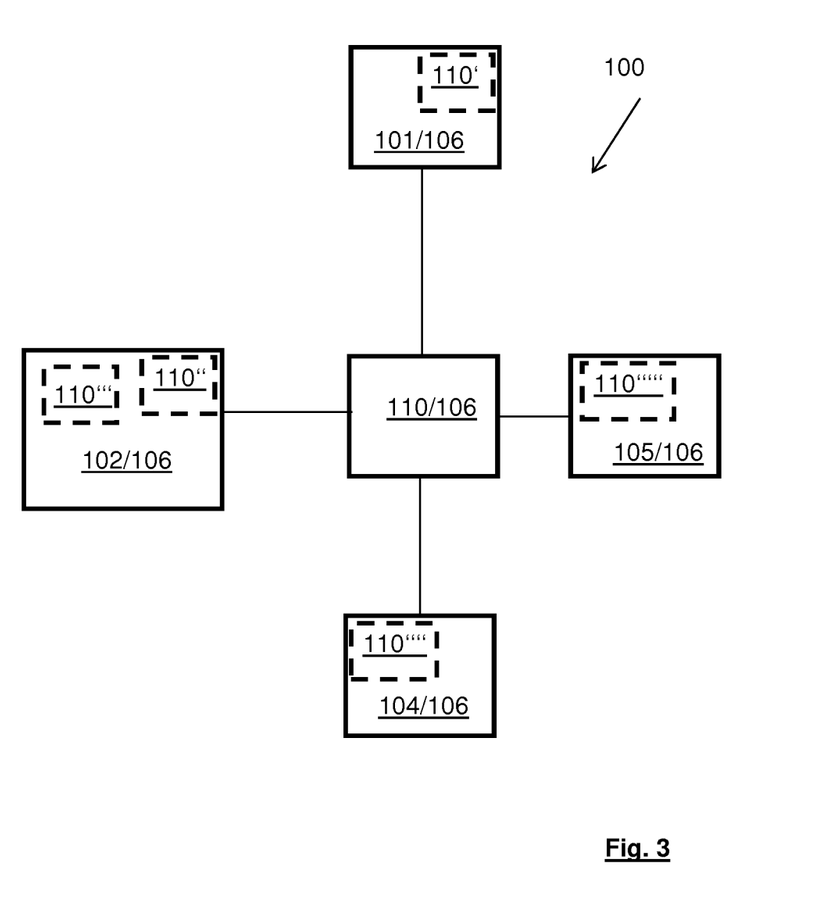
FIG. 3 a system for carrying out the method according to the invention.

FIG. 3 shows a system 100 for carrying out a method for the manufacture of a medical radiation protector 10, as exemplified in FIGS. 1 and 2. The system 100 comprises a scanner 101, a device for carrying out an additive manufacturing method 102 (in short: device 102) configured to process a plastic approved for medical use in/at/on a human or animal body, a screen 104 and a communication interface 105 for communication with a user, and a computer unit 110 connected to the scanner 101, the device 102, the screen 104 and the communication interface 105 (together also referred to as components 106) at least for the purpose of data exchange.

The scanner 101 is used to perform a light-based measurement of a patient's oral cavity and is designed, for example, as a laser scanner or LED scanner. The device for carrying out the additive manufacturing method 102 is preferably a device for the layered application of material or a device for the trackwise application of material or the application of material in lines, but also devices can be used which work according to other principles of the additive manufacturing method, especially if they are able to process plastics. The communication interface 106 for communication with the user can be the screen 104 combined with a keyboard and a computer mouse. Alternatively or additionally, a touchscreen can be provided, wherein of course also the screen 104 can be a touchscreen. Alternatively or additionally, acoustic communication options can be provided: loudspeaker, microphone and speech recognition software. Computer unit 110 is configured to execute the program units of a computer program or, more precisely, functions of these program units, wherein the computer program serves to perform the method of manufacturing the radiation protector 10, and by this computer program the components 101, 102, 103, 104 of system 100 are controlled and data transmitted by the components are processed. The computer unit 110 can be part of a computer, laptop, etc., but it can also be split into individual sub-units 110', 110", 110''', 110'''', 110''''' (indicated by dashed lines), which can be integrated in various components 106 of the system For example, sub-units 11", which serve to control the scanner 102 and/or process the scanner data, are then integrated into the scanner 102. Sub-units 11'''' which are used to control the additive manufacturing method on the corresponding device 102 and/or sub-units 110''' which are used to transform a 3D model or 3D solid model into a control file are then integrated into the device 102, for example.

Figure 4:
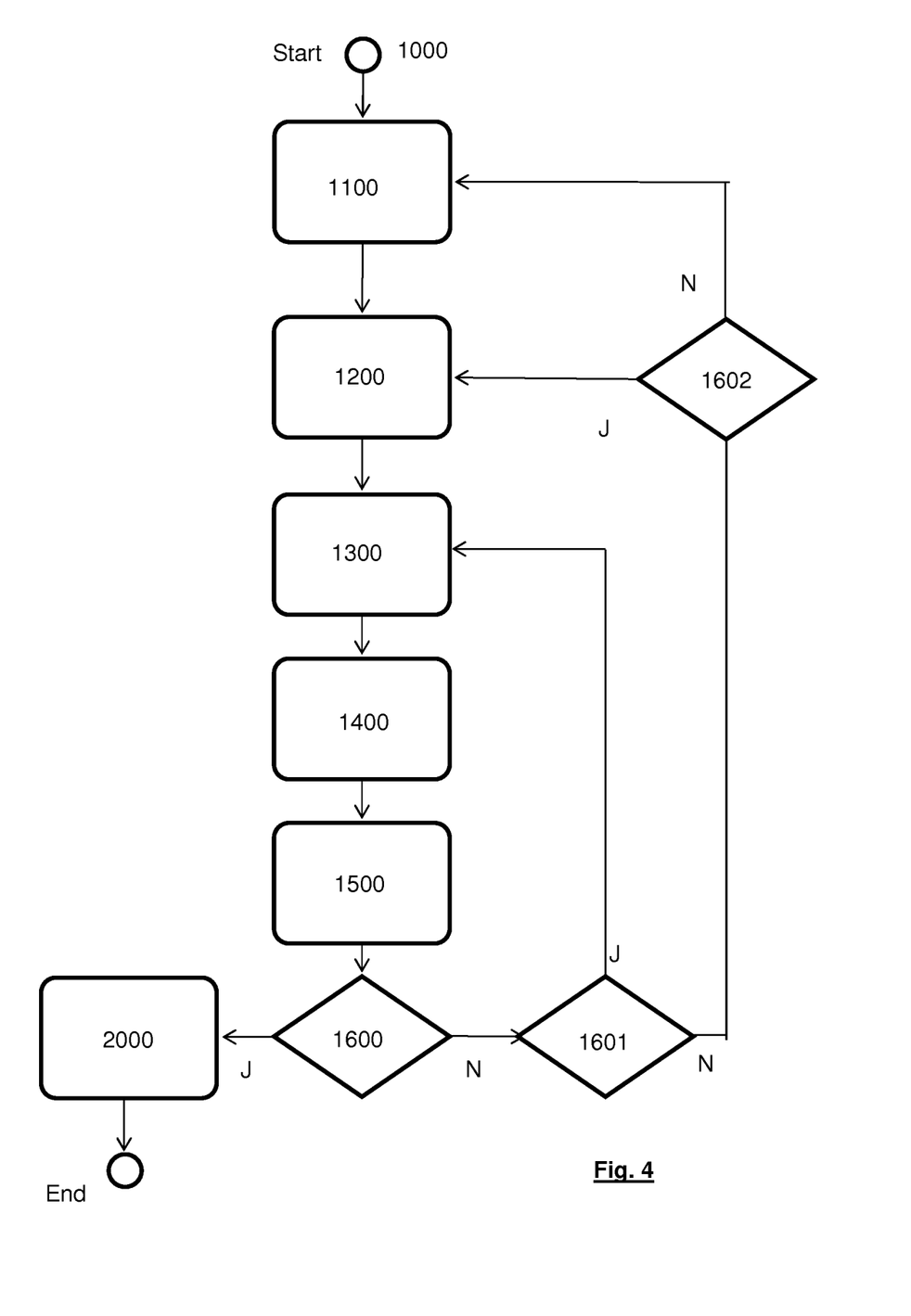
FIG. 4 a diagram of the manufacturing method according to the invention.

FIG. 4 shows schematically the main steps of a manufacturing method 1000 according to the invention for the production of a medical radiation protector, as was exemplified on the basis of FIGS. 1 and 2. In a first step, a suitably designed scanner is used to measure the three dimensions of a patient's oral cavity using a light-based measurement method (step 1100) (see also FIG. 5). Such methods can be based, for example, on the principle of transit time measurement or triangulation, etc. From the resulting scanner data, a 3D image file of the surfaces of the patient's oral cavity is generated in the computer unit 110 (step 1200; see also FIG. 6). From the 3D image data of this 3D image file, for example, a 3D image can be displayed on the screen 102 for quality control and can be viewed from all sides on the screen.

Figure 7:
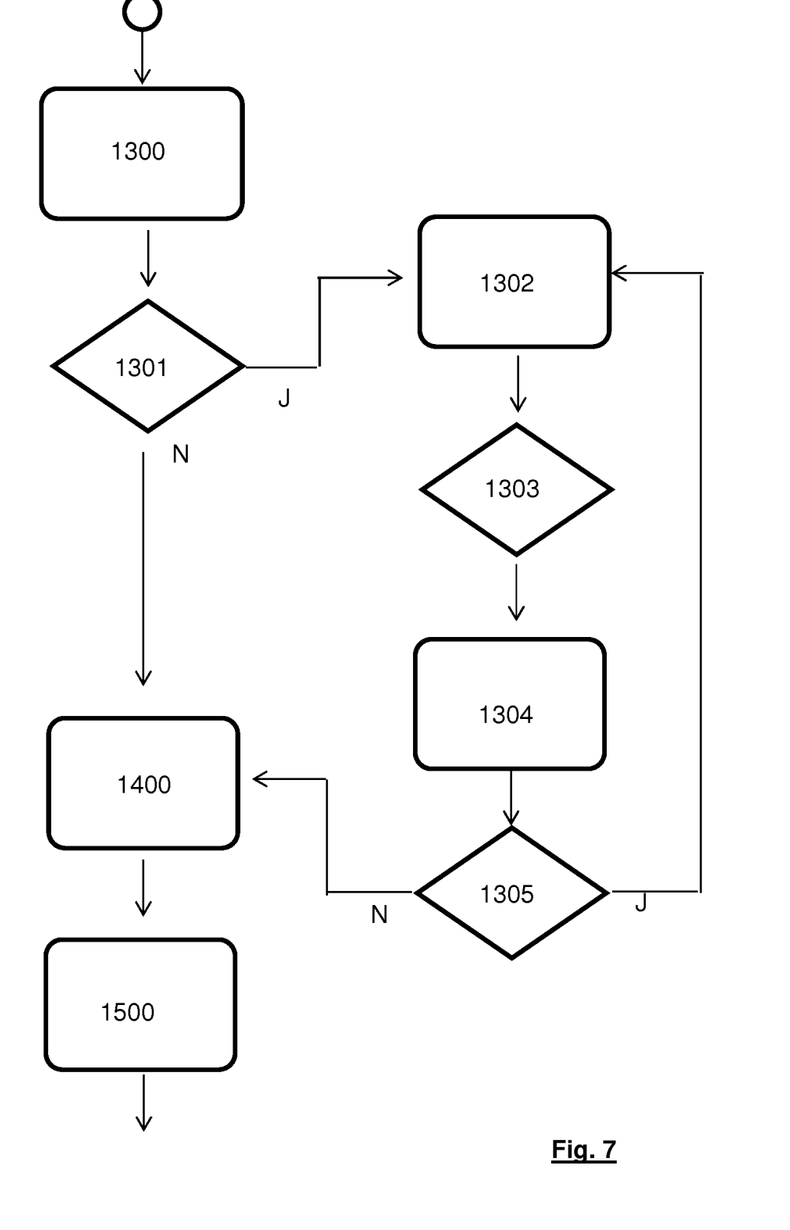

In a further step, the computer unit 110 automatically generates a virtual 3D solid model of the radiation protector from the data of the 3D image file (step 1300; see also FIGS. 7 and 8), which can naturally also be displayed on a screen and viewed from all sides on the screen. Within this method step 1300, it is optionally possible by manual intervention to adapt the virtual 3D solid model of the radiation protector to the individual needs of the patient and his/her treatment with the aid of the computer unit (see also FIGS. 7 and 8). The resulting virtual 3D model or 3D solid model of the radiation protector is then transformed into a control file for controlling a device to perform an additive manufacturing method (step 1400). Finally, the device 102 loaded with the necessary materials is controlled by means of the control file so that the radiation protector is produced with device 102 in an additive manufacturing method (step 1500). After quality control, during which it is checked whether the radiation protector fits well and can fulfil all its functions (step 1600), the radiation protector is either used in the radiation treatment (step 2000) or it is checked whether the 3D solid model or the 3D model of the radiation protector was defective (step 1601) or the 3D image file of the surfaces of the patient's oral cavity was defective (step 1602). If the 3D model was defective, one returns to step 1300 and generates a new 3D model by reworking the old one. If the 3D image file was already defective, one either goes back to step 1200 and generates a new 3D image file by editing the old data or creates a new scan and goes back to step 1100 if it is recognizable that a revision of the 3D image file is insufficient.

Figure 5:
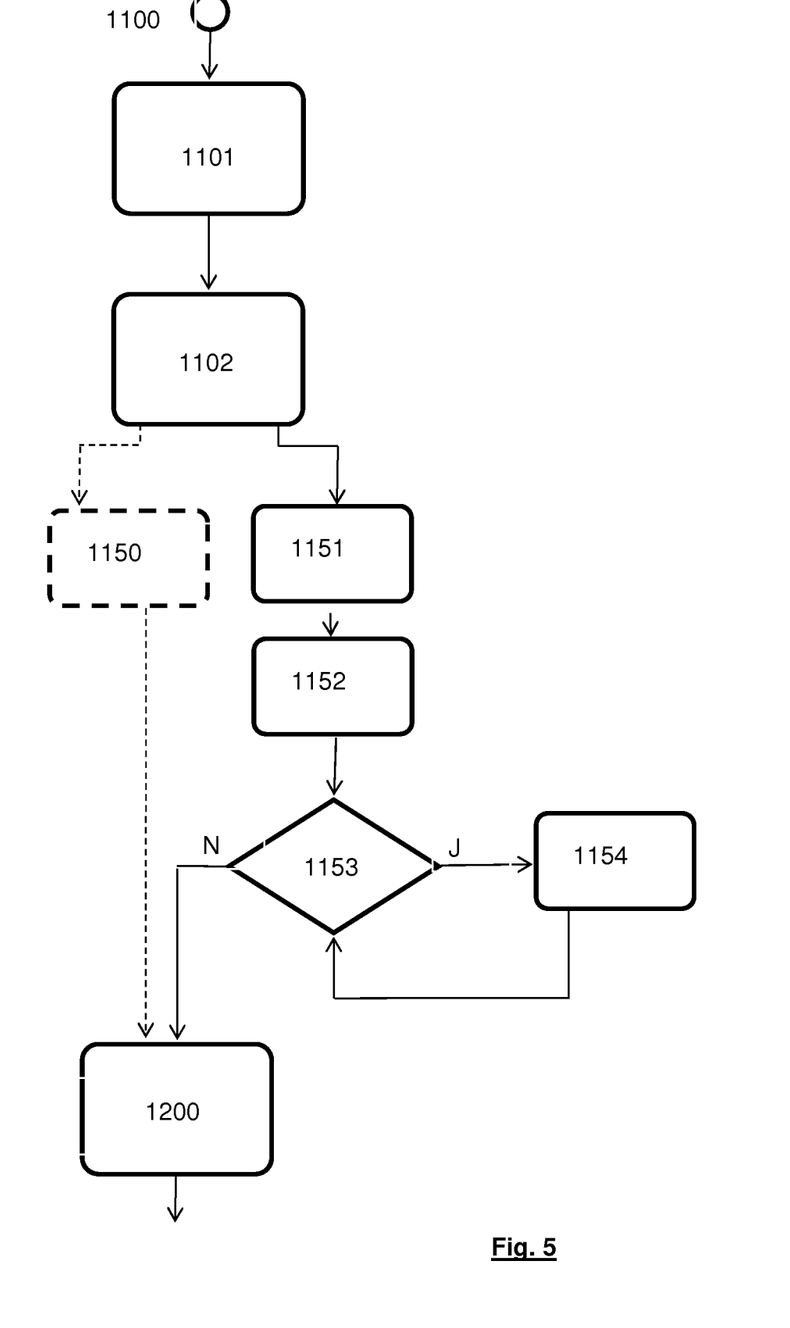
FIGS. 5 to 8 different steps of the method in detailed form.

Step 1100, scanning, can be explained in more detail using FIG. 5. All objects used for the scan in the patient's mouth should of course be disinfected (step 1101). Spreading elements or a retractor are then inserted into the patient's open mouth, stabilizing the patient's upper and lower jaws in a spread and well-defined position (step 1102). The scanner is then inserted into the patient's open mouth and the oral cavity can be scanned in a single step 1150 (indicated by dashed lines) or—depending on the scanner, the required data and the anatomy—in several steps, e.g. first scan of the upper jaw 1151, then scan of the lower jaw 1152 (or vice versa), and then possibly (decision 1153) separate scan 1154 of a cheek pocket or the spreading elements or the parts of the retractor located in the mouth and possibly other surfaces in the oral cavity (loop 1153/1154) until all desired surfaces have been scanned. For these separate scans it may be necessary, depending on the scanner and surface, to reposition the scanner or to use further/other spreading elements retractors. Once all necessary scans have been made, all foreign objects are removed from the patient's mouth. The scanner data obtained from the scan(s) is then used to generate a 3D image of the scanned surfaces 1200, which can be displayed on the screen (not shown), or a 3D image file with the corresponding 3D image data.

The scanner data as well as the original 3D image file generated from this data can be optionally saved (not shown).

Figure 6:
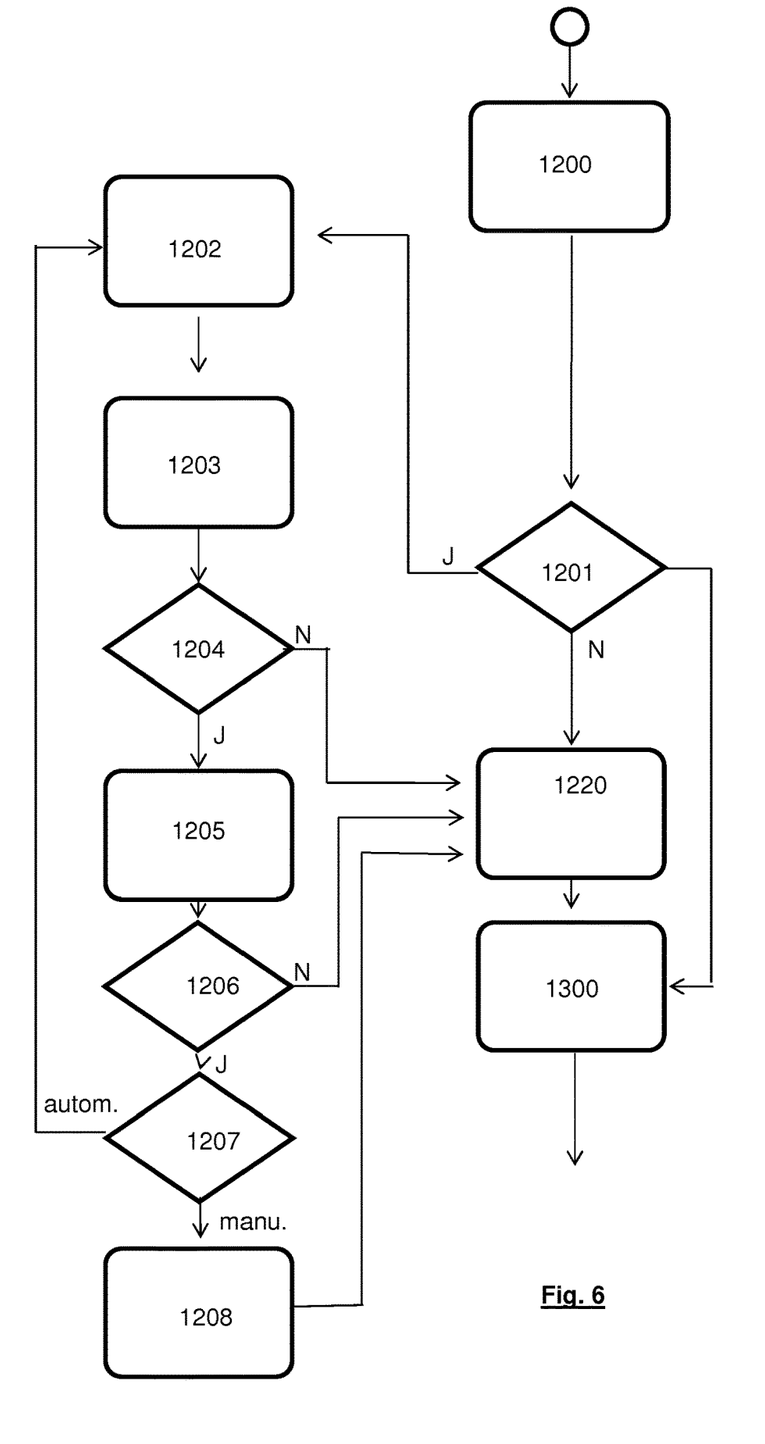

A solid model can be generated from the data of the 3D image file (decision 1201) without further optimization, see FIG. 6, but it has been shown that it is advantageous for a higher quality (decision 1201) to subject the image data to an optimization process, which can be carried out automatically by the computer unit, wherein at least superfluous data, e.g. those identified as measurement errors or those that were previously defined as not required for the design of the solid model, are ignored 1202 and obviously missing data are added 1203 (e.g. missing points in a point cloud by approximation processes), wherein steps 1202, 1203 are carried out in a result-oriented sequence. Further steps such as noise elimination, data smoothing etc. can be used for optimization. The result can be displayed on a screen 1205 (decision 1204) and on the basis of the image the user can decide whether to further optimize or not (decision 1206), and if so (decision 1207) whether to optimize manually (marked with manual) or in another automatic optimization process (marked with automatic). If optimization is to be carried out automatically, certain parameters of the automatic optimization process can be newly determined and the automatic optimization process is repeated 1202, 1203,

1204. If optimization is to be carried out manually 1208, this can be done on the screen via the corresponding communication interface (not shown in detail), wherein preferably possible tools, such as deleting or adding image elements, smoothing, generating gradients, etc. can be suggested and selected via the communication interface. If no further optimization is required—either manually or automatically—the optimization process is completed and the resulting 3D image file 1220 is used to generate the 3D solid model of the radiation protector 1300. The resulting 3D image file 1220 can optionally be saved (not displayed).

A virtual upper jaw impression and a virtual lower jaw impression are generated for the generation of the 3D solid model, from which the tooth rests 28, 32 are then scored. Furthermore, the virtual impressions are joined together in such a way that the virtual upper jaw impression and virtual lower jaw impression coincide anatomically, so that upper and lower jaw elements can be generated anatomically in the correct position. Optionally, at least one virtual tissue protection element 70 is also generated, wherein radiation protectors with tissue protection elements frequently required in a given position can also be preset as standard, so that these can be selected beforehand and together with the upper jaw element 20/26 and the lower jaw element 30 can be generated automatically by the computer unit as a defined type of radiation protector.

Otherwise, the virtual tissue protection elements 70 can also be added by a corresponding selection procedure (see FIGS. 7 and 8) after the automatic generation of the virtual upper jaw element 20/26 and lower jaw element 30. The virtual upper jaw 20/26 and lower jaw elements 30 and the optional at least one virtual tissue protection element 70 are joined together to form a virtual 3D model of the virtual radiation protector 10 in such a way that upper jaw and lower jaw elements 20/26, 30 coincide with each other anatomically and all optional further virtual elements are in the anatomically correct position or in the position necessary for treatment with respect to the virtual upper jaw and lower jaw elements 20/26, 30.

The 3D solid model of the radiation protector (see FIGS. 7, 8) generated from the original 3D image file or from the 3D image file 1220 resulting from the optimization process (step 1300) can comprise only the virtual upper and lower jaw elements 20726, 30 as described above, or a certain tissue protection element 70 as standard. The 3D solid model can either (decision 1301) be directly converted into a control file 1400 or it can be further processed, for example to adapt it to the individual needs of the patient and his or her treatment, or to eliminate any errors during model generation. For this purpose, the 3D solid model of the radiation protector can of course be displayed on a screen (not shown). For further processing (see FIG. 7) a complete toolbox can be made available via a communication interface 1302, from which the corresponding element is then selected 1303 in order to then insert it 1304. After completion of this step it can be decided in each case 1305 whether further machining is desired and the tool selection 1302 is returned Y or whether the machining is completed N and a control file is to be generated from the existing 3D model of the radiation protector 1400 for carrying out the additive manufacturing method 1500 on the device 102. The generated 3D model is preferably saved (not displayed).

When manually adapting the 3D solid model to the individual needs of the patient and his or her treatment, the computer unit 110 offers a selection of manually selectable options for machining on 1302, so-called tools, by means of a communication interface 106. The selection includes at least one or more of the following options: Creating a tissue protection element; creating a tongue positioner, creating a cheek positioner, creating a lip positioner, creating a mouthguard, creating a catheter, creating a pocket-like recess; machining a lower jaw element, machining an upper jaw element, machining a tissue protection element; machining a tongue positioner, machining a cheek positioner, machining a lip positioner, machining a toothguard, machining a catheter, machining a pocket-like recess; machining the surface. Tools for machining can be moving, enlarging, reducing, polishing, smoothing, etc.

Figure 8:
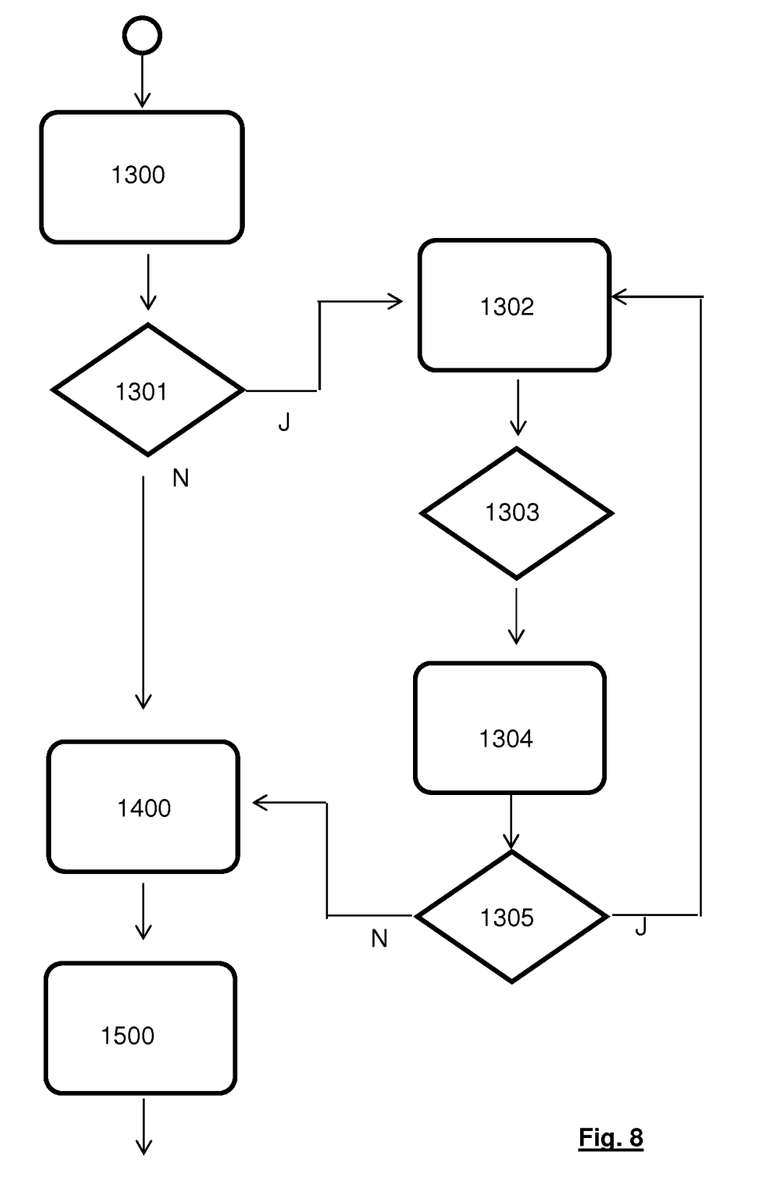

As shown in FIG. 8, these tools can also be offered in hierarchical order 1530, so that the first decision is 1351 whether a new tissue protection element is generated E or whether an existing element is to be machined B. Then the desired tool is selected from a selection of tools provided for machining 1370 or a desired element is selected 1371 or 1381 from a selection of producible elements 1380, the element is positioned accordingly 1382 in relation to upper and lower jaw element respectively 1372 and then it is decided whether the machining should be continued by returning to selection menu 1350 or whether the machining is finished and a control file should be generated from the virtual 3D model of the radiation protector 1400. The generated 3D model is preferably saved (not displayed). The control file finally controls the additive manufacturing method on device 102, so that it can be executed 1500 and from the virtual 3D model of the radiation protector the real radiation protector 10 is created.

In the additive manufacturing method, step 1500, preferably a plastic approved for the corresponding medical purpose is applied in layers or in individual material lines or material tracks. Depending on the specific design of the method, a supporting structure may have to be erected before and/or during the application of the material, which may have to be removed later. Depending on the choice of material, the plastic may also have to cure, which may occur due to UV or temperature or due to the components of the plastic without further intervention. Also depending on the method, the surface of the radiation protector may have to be treated, in particular deburred (in the case of support constructions) or grinded/polished before use by the patient. Some known processes (no conclusive list) which can be used here (no conclusive list) are briefly outlined below, wherein the term material is of course primarily—but not exclusively (in certain processes different materials can also be combined, the person skilled in the art recognizes this)—the plastic described above:

Powder-binding process: The material is applied in powder form in layers to a carrier plate by means of a roller and solidified along pre-programmed lines by adding a second component—a binder. The carrier plate is lowered and a new powder layer is applied by means of a roller. These steps are repeated until the desired item is finished. The non-hardened powder is removed and can be used without further treatment for the production of the next item.

Selective laser sintering: Similar to powder binding, but the powder is partially melted or melted along pre-programmed lines using a laser beam.

Multi-Jet Modeling (MJM); Polyjet: Selective laser melting, layer by layer application of the liquid, light-curing polymer material onto a lowering carrier plate by means of heated application heads. Curing is carried out each time a new layer is applied using a UV lamp.

Fused Deposition Modeling (FDM): Wire-shaped starting material (e.g. plastic "wire") wound onto a coil is liquefied in a heated application nozzle and applied first to the heated carrier platform and then in layers to the underlying layers of material.

ARBURG® Freeform shaping of plastics

Similar to FDM, but instead of plastic "wire", plastic granulate is used, which is melted and applied layer by layer, droplet by droplet, to a carrier plate that can move in 3 to 5 dimensions. The application nozzle is stationary in this case.

The person skilled in the art is aware that and in what way the embodiments described or the details described on the basis of the exemplary embodiments can be combined sensibly. For space reasons, however, it is not possible to represent and/or describe all possible and meaningful combinations in detail.

The invention claimed is:

1. A method for manufacturing a radiation protector comprising:
    measuring, by a scanner including a light-based measurement, a patient's oral cavity in three dimensions (3D) to create a 3D computer model of the oral cavity;
    generating, a 3D image file of surfaces of the patient's oral cavity from resulting scanner data by a computer, wherein based on the 3D image file a 3D image is displayable on a screen associated with the computer;
    generating, from the 3D image file or the 3D image of the surfaces of the patient's oral cavity a virtual 3D solid model of the radiation protector via the computer;
    transforming the virtual 3D solid model into a control file for controlling a device; and
    providing the device with the control file to produce the radiation protector according to the control file.

2. The method according to claim 1, wherein
a plastic is applied in layers or in individual material lines during production of the radiation protector.

3. The method according to claim 1, wherein
the 3D image file or the 3D image is optimized with the computer by adding missing data and disregarding incorrect measured values.

4. The method according to claim 1, comprising
scanning upper and lower jaws of the patient separately, and wherein the scanner data from which the 3D image file is generated is combined by the computer such that an upper jaw image and a lower jaw image coincide with each other anatomically in the 3D image.

5. The method according to claim 1, comprising
generating a virtual upper jaw element and a virtual lower jaw element by the computer for the generation of the virtual 3D solid model, and at least one virtual tissue protection element, and wherein the virtual upper jaw element and the virtual lower jaw element and the at least one virtual tissue protection element are combined to form the virtual 3D solid model such that the virtual upper jaw element and the virtual lower jaw element coincide with each other anatomically.

6. The method according to claim 1, comprising adapting the virtual 3D solid model to individual patient requirements based on feedback sent to the computer, which offers options via a communication interface, wherein the options comprise at least one or more of, which are optionally offered in hierarchical order, creating a tissue protection element, creating a tongue positioner, creating a cheek positioner, creating a lip positioner, creating a mouthguard, creating a catheter, creating a pocket-like recess, machining a lower jaw element, machining an upper jaw element, machining a tissue protection element, machining a tongue positioner, machining a cheek positioner, machining a lip positioner, machining a mouthguard, machining a catheter, machining a pocket-like recess, machining the surface, and wherein at least one or more of the following options are available as a selection for machining: moving, enlarging, reducing, polishing, smoothing, deburring, joining.

7. A non-transitory computer program product having program code stored on a machine-readable medium that when executed causes a processor to perform:
    controlling a scanner measuring an oral cavity of a patient in three dimensions (3D) to create a 3D computer model of the oral cavity; creating a 3D image file or a 3D image of a surface of the patient's oral cavity, with optimized 3D image data based on the measuring of the oral cavity;
    creating a virtual 3D solid model of a radiation protector from the 3D image file or the 3D image or the optimized 3D image data;
    transforming the virtual 3D solid model of the radiation protector into a control file to control a device to manufacture the radiation protector; and transferring the control file to a device to perform the manufacturing of the radiation protector.

8. A system comprising:
    a scanner configured to measure a patient's oral cavity to create a virtual three-dimensional (3D) model of the oral cavity;
    a device configured to manufacture a radiation protector via a plastic;
        a computer communicatively coupled to the scanner and the device comprising a display screen and a communication interface, and configured to receive the virtual 3D model and transform the virtual 3D model into a control file, and wherein
    the device is configured to manufacture the radiation protector based on the control file.

9. A system according to claim 8, wherein
the computer
is configured to control the scanner and process the scanner data, and transform the virtual 3D model into a control file.

10. The system according to claim 8, wherein
the device is further configured to apply material in layers or tracks or in lines.

11. The system according to claim 8, wherein
the scanner is configured to perform a light-based measurement comprising an LED scanner or a laser scanner.

12. A radiation protector comprising:
a lower jaw element; and
an upper jaw element affixed to the lower jaw element via sidewalls extending vertically from the lower jaw element to the upper jaw element, and wherein at least one of the sidewalls includes one or more of a pocket shaped recess and a catheter channel.

13. A radiation protector according to claim 12, wherein one or more of the upper jaw element and the lower jaw element comprise a tissue protection element selected from the group consisting of: a tongue positioner, a cheek positioner, a lip positioner, a mouthguard, a catheter, a pocket-like recess for receiving another material.

14. The radiation protector according to claim 12, wherein the upper jaw element and the lower jaw element are produced in layers by an additive procedure.

15. The radiation protector according to claim 14, wherein the additive procedure includes individual material lines or individual material tracks.

16. The radiation protector according to claim 12, wherein one or more of the upper jaw element and the lower jaw element comprises
plastic material, and at least one other material from the following group: another plastic, a radiation-shielding material, and a radiant material.

17. The radiation protector according to claim 12, wherein at least the upper jaw element and lower jaw element are one material.

18. The radiation protector according to claim 13, wherein the upper jaw element the lower jaw element and the tissue protection element are one continuous piece.

* * * * *